(12) United States Patent
Blaskovich et al.

(10) Patent No.: US 8,932,618 B2
(45) Date of Patent: *Jan. 13, 2015

(54) BIODEGRADABLE OSMOTIC PUMP IMPLANT FOR DRUG DELIVERY

(71) Applicant: Covidien LP, Mansfield, MA (US)

(72) Inventors: Phillip D. Blaskovich, Salem, MA (US); Rachit Ohri, Framingham, MA (US); Steven L. Bennett, Cheshire, CT (US)

(73) Assignee: Confluent Surgical, Inc., Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/939,720

(22) Filed: Jul. 11, 2013

(65) Prior Publication Data

US 2013/0296833 A1   Nov. 7, 2013

Related U.S. Application Data

(63) Continuation of application No. 12/974,394, filed on Dec. 21, 2010, now Pat. No. 8,518,440.

(51) Int. Cl.
 *A61F 13/00* (2006.01)
 *A61F 2/00* (2006.01)
 *A61K 9/52* (2006.01)
 *A61K 9/14* (2006.01)
 (Continued)

(52) U.S. Cl.
 CPC .............. *A61K 9/0004* (2013.01); *A61K 9/0024* (2013.01)
 USPC ........... 424/422; 424/423; 424/486; 424/457; 604/892.1

(58) Field of Classification Search
 CPC ... A61K 9/0024; A61K 31/74; A61K 31/765; A61K 47/30; A61K 47/34; A61K 2201/21; A61K 2201/30
 USPC ................ 604/892.1; 424/422, 423, 486, 457
 See application file for complete search history.

(56) References Cited

U.S. PATENT DOCUMENTS

| 4,200,098 A | 4/1980 | Ayer et al. |
|---|---|---|
| 4,235,236 A | 11/1980 | Theeuwes |
| 4,327,725 A | 5/1982 | Cortese et al. |

(Continued)

FOREIGN PATENT DOCUMENTS

| EP | 1 967 220 A2 | 9/2008 |
|---|---|---|
| EP | 2 143 737 A1 | 1/2010 |

(Continued)

OTHER PUBLICATIONS

Extended European Search Report from Application No. EP 11194491.4 dated Dec. 3, 2013.

(Continued)

*Primary Examiner* — Blessing M Fubara
(74) *Attorney, Agent, or Firm* — Carter DeLuca Farrell & Schmidt LLP

(57) ABSTRACT

The present disclosure relates to a drug delivery device including a biodegradable housing and a hydrogel within the biodegradable housing. The housing, the hydrogel, or both, may include a bioactive agent. Also disclosed is a method of drug delivery including the steps of forming the biodegradable housing, in embodiments a hydrogel, suspending a bioactive agent in the hydrogel, and introducing a second hydrogel and/or precursors of a second hydrogel into the biodegradable housing.

18 Claims, 5 Drawing Sheets

(51) Int. Cl.
*A61K 9/22* (2006.01)
*A61K 9/00* (2006.01)

(56) References Cited

U.S. PATENT DOCUMENTS

| | | | |
|---|---|---|---|
| 4,359,049 A | 11/1982 | Redl et al. |
| 4,631,055 A | 12/1986 | Redl et al. |
| 4,735,616 A | 4/1988 | Eibl et al. |
| 4,783,337 A | 11/1988 | Wong et al. |
| 4,874,368 A | 10/1989 | Miller et al. |
| 4,902,281 A | 2/1990 | Avoy |
| 4,932,942 A | 6/1990 | Maslanka |
| 4,978,336 A | 12/1990 | Capozzi et al. |
| 5,000,957 A | 3/1991 | Eckenhoff et al. |
| 5,116,315 A | 5/1992 | Capozzi et al. |
| 5,162,430 A | 11/1992 | Rhee et al. |
| 5,324,775 A | 6/1994 | Rhee et al. |
| 5,410,016 A | 4/1995 | Hubbell et al. |
| 5,514,379 A | 5/1996 | Weissleder et al. |
| 5,543,441 A | 8/1996 | Rhee et al. |
| 5,550,187 A | 8/1996 | Rhee et al. |
| 5,752,974 A | 5/1998 | Rhee et al. |
| 5,840,338 A | 11/1998 | Roos et al. |
| 5,874,500 A | 2/1999 | Rhee et al. |
| 6,030,442 A | 2/2000 | Kabra et al. |
| 6,152,943 A | 11/2000 | Sawhney |
| 6,165,201 A | 12/2000 | Sawhney et al. |
| 6,179,862 B1 | 1/2001 | Sawhney |
| 6,514,534 B1 | 2/2003 | Sawhney |
| 6,566,406 B1 | 5/2003 | Pathak et al. |
| 6,605,294 B2 | 8/2003 | Sawhney |
| 6,656,200 B2 | 12/2003 | Li et al. |
| 6,673,093 B1 | 1/2004 | Sawhney |
| 6,703,047 B2 | 3/2004 | Sawhney et al. |
| 6,706,283 B1 | 3/2004 | Appel et al. |
| 6,753,011 B2 | 6/2004 | Faour |
| 6,818,018 B1 | 11/2004 | Sawhney |
| 6,887,974 B2 | 5/2005 | Pathak |
| 7,009,034 B2 | 3/2006 | Pathak et al. |
| 7,074,423 B2 | 7/2006 | Fereira et al. |
| 7,332,566 B2 | 2/2008 | Pathak et al. |
| 7,347,850 B2 | 3/2008 | Sawhney |
| 7,361,168 B2 | 4/2008 | Makower et al. |
| 7,534,241 B2 | 5/2009 | Coppeta et al. |
| 8,518,440 B2 * | 8/2013 | Blaskovich et al. .......... 424/457 |
| 2001/0046518 A1 | 11/2001 | Sawhney |
| 2002/0091448 A1 | 7/2002 | Atala |
| 2004/0197374 A1 | 10/2004 | Rezania et al. |
| 2005/0276841 A1 | 12/2005 | Davis et al. |
| 2007/0031496 A1 | 2/2007 | Edgren et al. |
| 2007/0116765 A1 | 5/2007 | Hu et al. |
| 2007/0293885 A1 | 12/2007 | Binmoeller |
| 2008/0114092 A1 | 5/2008 | Sawhney |
| 2008/0220047 A1 | 9/2008 | Sawhney et al. |
| 2009/0005763 A1 | 1/2009 | Makower et al. |
| 2009/0227689 A1 | 9/2009 | Bennett |
| 2009/0227981 A1 | 9/2009 | Bennett |

FOREIGN PATENT DOCUMENTS

| | | |
|---|---|---|
| EP | 2179753 A2 | 4/2010 |
| EP | 2 196 193 A1 | 6/2010 |
| EP | 2 233 160 A2 | 9/2010 |
| EP | 2 233 161 A2 | 9/2010 |
| EP | 2389926 A2 | 11/2011 |
| WO | 00/44808 A1 | 8/2000 |

OTHER PUBLICATIONS

Vasir et al. "Bioadhesive microspheres as a controlled drug delivery system" in International Journal of Pharmaceutics vol. 255, Issues 12, Apr. 14, 2003, pp. 13-32.
Zelenetskii et al. "Some problems of the development of syringes made of polymer materials," in All Union Scientific Research Institute of Polymers, Moscow, Mar.-Apr. 1972.
International Search Report issued in Application EP 11250562.3 mailed Dec. 8, 2011.
International Search Report issued in Application EP 11250564.9 mailed Dec. 8, 2011.
International Search Report issued in Application EP 11250563.1 mailed Dec. 27, 2011.
International Search Report issued in Application EP 11250566.4 mailed Dec. 22, 2011.
International Search Report issued in Application EP 11250565.6 mailed Dec. 23, 2011.

* cited by examiner

BIODEGRADABLE OSMOTIC PUMP IMPLANT FOR DRUG DELIVERY

CROSS-REFERENCE TO RELATED APPLICATIONS

This application is a continuation of U.S. patent application Ser. No. 12/974,394, filed Dec. 21, 2010, now U.S. Pat. No. 8,518,440, the entire disclosure of which is incorporated by reference herein.

BACKGROUND

The present disclosure is related to hydrogels for use in drug delivery. The hydrogels may provide for the controlled release of a drug.

Hydrogels may be utilized for the delivery of therapeutic agents such as drugs. Drugs may be released by diffusion through a hydrogel to the surrounding tissue, degradation of the hydrogel itself, or a combination of both diffusion and degradation. Drug release may be influenced by formulation variables such as the physicochemical properties of the drug, including drug solubility, and the method of drug incorporation in the hydrogel, e.g., the use of encapsulation vehicles like microspheres or microcapsules.

Other means for drug delivery are within the purview of those skilled in the art, and include those which try to provide a more controlled release of a drug. For example, implantable pumps may be utilized to achieve more controlled drug delivery. However, one issue with implantable pumps is they require surgical intervention for removal when the drug has been expended.

It would be advantageous to be able to modulate drug release profiles without having to manipulate the drug molecule or compound, and without the use of excipients. A biodegradable osmotic pump which would avoid the need for repeated surgical intervention would also be beneficial.

SUMMARY

The present disclosure provides drug delivery devices and methods for making and using same. In embodiments, a drug delivery device of the present disclosure includes a housing including a polymeric material; and a biodegradable hydrogel within the housing; wherein the polymeric material, the biodegradable hydrogel, or both, includes a bioactive agent.

Methods of drug delivery in accordance with the present disclosure include, for example, forming a housing including a polymeric material in situ; introducing at least one bioactive agent and precursors comprising a biodegradable hydrogel into the housing; and allowing the precursors to form the biodegradable hydrogel within the housing. In other embodiments, the housing may be formed ex vivo, with the introduction of the biodegradable hydrogel and/or bioactive agent occurring ex vivo, in situ, or both.

BRIEF DESCRIPTION OF DRAWINGS

Various embodiments of the present disclosure will be described herein below with reference to the figures wherein.

DETAILED DESCRIPTION

Figure 1:
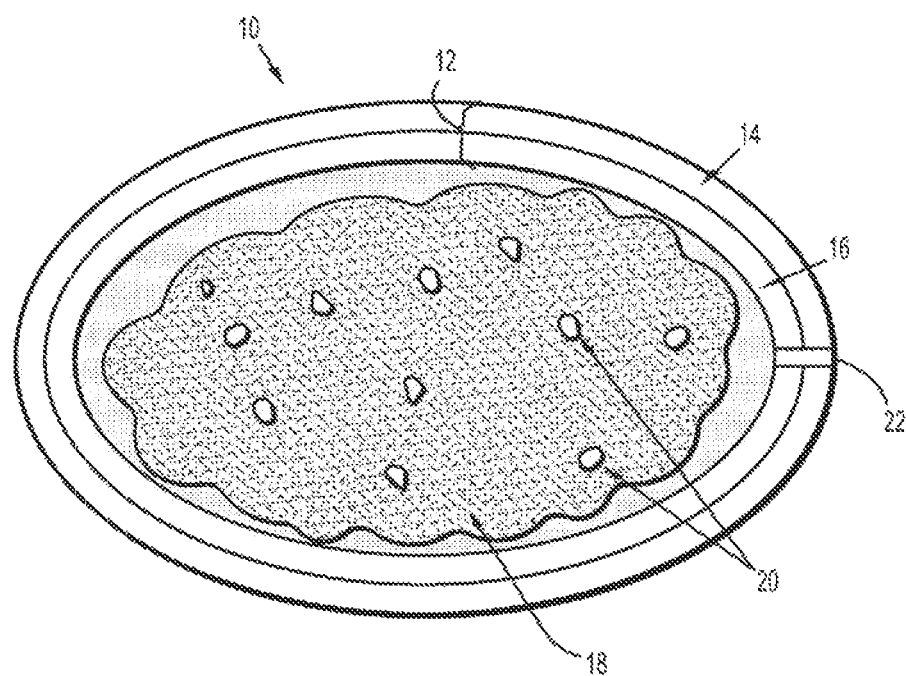
FIG. 1 represents an embodiment of an osmotic pump of the present disclosure.

The present disclosure provides a device for delivery of a bioactive agent. In embodiments, the device includes an osmotic pump, which may include at least one hydrogel. The device of the present disclosure may degrade in situ. Thus, unlike other implantable osmotic pumps, the present pump does not require surgical intervention for removal. In embodiments, an osmotic pump of the present disclosure may include a housing and a hydrogel within the housing. In embodiments, utilizing a hydrogel of the present disclosure, prolonged and/or expedited release of a bioactive agent may be achieved in a controlled manner.

The osmotic pump of the present disclosure may include two components, both a biodegradable housing and a hydrogel "pump" within the housing. In embodiments the housing, the pump, or both, may include a bioactive agent. The biodegradable housing of the osmotic pump acts as a shell or frame around the hydrogel pump. In embodiments, the biodegradable housing may be semi-permeable or impermeable.

The housing may be formed in vivo, or the housing may be formed ex vivo, and subsequently introduced in vivo. In embodiments, the housing of the osmotic pump may be formed ex vivo, and then introduced into a patient. For example, a hydrogel may be formed, optionally dehydrated, and the dehydrated or hydrated hydrogel may then be introduced into a patient. Alternatively, the hydrogel forming the housing may be formed in vivo.

However formed, the hydrogel forming the housing, sometimes referred to herein as a "pouch," may then be filled with a second hydrogel, in embodiments containing a bioactive agent. The second hydrogel may be introduced into the pouch ex vivo or in vivo.

Hydrogel Systems Overview

In embodiments, components which may be utilized for forming hydrogels and hydrogel-based housings utilized to form an osmotic pump of the present disclosure include in situ forming material(s), which may include a single precursor or multiple precursors. These precursor(s) may form "in situ", meaning formation occurs in a living animal or human body. In general, this may be accomplished by utilizing precursors that can be activated at the time of application to tissue to form an in situ forming material, in embodiments a hydrogel. In other embodiments, at least one of the precursors may be formed "ex vivo," meaning formation occurs outside a living animal or human body.

In situ forming materials may be formed either through covalent, ionic or hydrophobic bonds. Physical (non-covalent) crosslinks may result from complexation, hydrogen bonding, desolvation, Van der Waals interactions, ionic bonding, combinations thereof, and the like, and may be initiated by mixing two precursors that are physically separated until combined in situ, or as a consequence of a prevalent condition in the physiological environment, including temperature, pH, ionic strength, combinations thereof, and the like. Chemical (covalent) crosslinking may be accomplished by any of a number of mechanisms, including free radical polymerization, condensation polymerization, anionic or cationic polymerization, step growth polymerization, electrophile-nucleophile reactions, combinations thereof, and the like.

In some embodiments, components of the osmotic pump of the present disclosure may include biocompatible multi-precursor systems that spontaneously crosslink when the precursors are mixed, but wherein the two or more precursors are individually stable for the duration of the deposition process. Such systems include, for a hydrogel, a first precursor including macromers that are di- or multifunctional amines, and a second precursor including di- or multifunctional oxirane containing moieties.

Some embodiments of forming components of the osmotic pump of the present disclosure involve mixing precursors that quickly crosslink. The crosslinking reaction leading to gelation can occur, in some embodiments, within a time from about 1 second to about 5 minutes, in embodiments from about 3 seconds to about 1 minute; persons of ordinary skill in these arts will immediately appreciate that all ranges and values within these explicitly stated ranges are contemplated. In some cases gelation may occur in less than 10 seconds.

The precursors may be placed into solution prior to use. Where two solutions are employed, each solution may contain one precursor of a component of the osmotic pump of the present disclosure material which forms upon on contact. The solutions may be separately stored and mixed when delivered to tissue to form the housing of an osmotic pump, the hydrogel within said housing, or both.

Additionally, any solutions utilized as part of the osmotic pump should not contain harmful or toxic solvents. In embodiments, the precursor(s) may be substantially soluble in a solvent such as water to allow application in a physiologically-compatible solution, such as buffered isotonic saline.

Properties of the hydrogels utilized in an osmotic pump may be selected according to the intended application. For example, for the hydrogel included within an osmotic pump, it may be desirable that the in situ forming material system undergo significant swelling and be biodegradable. Alternatively, for the in situ forming material utilized to form the housing of an osmotic pump, little or no swelling may be desired.

Other applications may require different characteristics. Generally, the materials should be selected on the basis of exhibited biocompatibility and lack of toxicity.

Certain properties of the materials utilized in forming an osmotic pump can be useful, including adhesion to a variety of tissues, desirable setting times, high water content for biocompatibility, which may be relevant for hydrogels, mechanical strength for use in forming the housing of an osmotic pump, and/or toughness to resist destruction after placement. Synthetic materials that are readily sterilized and avoid the dangers of disease transmission involved in the use of natural materials may thus be used. Indeed, certain hydrogels made using synthetic precursors are within the purview of those skilled in the art, e.g., as used in commercially available products such as FOCALSEAL® (Genzyme, Inc.), COSEAL® (Angiotech Pharmaceuticals), and DURASEAL® (Confluent Surgical, Inc). Other known hydrogels include, for example, those disclosed in U.S. Pat. Nos. 6,656,200; 5,874,500; 5,543,441; 5,514,379; 5,410,016; 5,162,430; 5,324,775; 5,752,974; 5,550,187; 6,566,406; 6,887,974; 7,009,034; and 7,332,566.

As noted above, the components of an osmotic pump of the present disclosure may be made from one or more precursors. The precursor may be, e.g., a monomer or a macromer. One type of precursor may have a functional group that is ethylenically unsaturated. An ethylenically unsaturated functional group may be polymerized using an initiator to start the reaction. Precursors with at least two ethylenically unsaturated functional groups may form crosslinked polymers. Some compositions have certain precursors with only one such functional group and additional crosslinker precursors with a plurality of functional groups for crosslinking the precursors. Ethylenically unsaturated functional groups may be polymerized by various techniques, e.g., free radical, condensation, or addition polymerization.

The components of an osmotic pump of the present disclosure may thus be formed from one precursor (as by free radical polymerization), two precursors, or made with three or more precursors, with one or more of the precursors participating in crosslinking to form the components of an osmotic pump of the present disclosure.

Other precursors which may be used to form a hydrogel may have a functional group that is an electrophile or nucleophile. Electrophiles react with nucleophiles to form covalent bonds. Covalent crosslinks or bonds refer to chemical groups formed by reaction of functional groups on different polymers that serve to covalently bind the different polymers to each other. In certain embodiments, a first set of electrophilic functional groups on a first precursor may react with a second set of nucleophilic functional groups on a second precursor. When the precursors are mixed in an environment that permits reaction (e.g., as relating to pH or solvent), the functional groups react with each other to form covalent bonds. The precursors become cross-linked when at least some of the precursors can react with more than one other precursor. For instance, a precursor with two functional groups of a first type may be reacted with a crosslinking precursor that has at least three functional groups of a second type capable of reacting with the first type of functional groups.

As noted above, the components of the osmotic pump may be a hydrogel. The hydrogel may be utilized to form the housing of an osmotic pump of the present disclosure, placed within such a housing, or both. In embodiments the hydrogel may be formed from single precursors or multiple precursors. For example, where the hydrogel is formed from multiple precursors, for example two precursors, the precursors may be referred to as a first and second hydrogel precursor. The terms "first hydrogel precursor" and "second hydrogel precursor" each mean a polymer, functional polymer, macromolecule, small molecule, or crosslinker that can take part in a reaction to form a network of crosslinked molecules, e.g., a hydrogel.

In other embodiments, the osmotic pump of the present disclosure may include an outer layer made of a polymeric material including, for example, oxidized cellulose, polylactide, polyglycolide, polylactide-co-glycolide copolymers, combinations thereof, and the like.

In embodiments, each of the first and second hydrogel precursors includes only one category of functional groups, either only nucleophilic groups or only electrophilic functional groups, so long as both nucleophilic and electrophilic precursors are used in the crosslinking reaction. Thus, for example, if the first hydrogel precursor has nucleophilic functional groups such as amines, the second hydrogel precursor may have electrophilic functional groups such as N-hydroxysuccinimides. On the other hand, if first hydrogel precursor has electrophilic functional groups such as sulfosuccinimides, then the second hydrogel precursor may have nucleophilic functional groups such as amines or thiols. Thus, functional polymers such as proteins, poly(allyl amine), styrene sulfonic acid, or amine-terminated di- or multifunctional poly (ethylene glycol) ("PEG") can be used.

The first and second hydrogel precursors may have biologically inert and water soluble cores. When the core is a polymeric region that is water soluble, suitable polymers that may be used include: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose, hydroxymethylcellulose, hyaluronic acid; and proteins such as albumin, collagen, casein, and gelatin. The polyethers, and more particularly poly(oxyalkylenes) or poly(ethylene glycol) or polyethylene glycol, may be utilized in some embodiments. Derivatives of the foregoing, as well as combinations thereof, may be utilized to form the core. When the core is small in molecular nature, any of a variety of hydrophilic functionalities can be used to make the first and second hydrogel precursors water soluble. In embodiments, functional groups like hydroxyl, amine, sulfonate and carboxylate, which are water soluble, maybe used to make the precursor water soluble. For example, the N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

In embodiments, at least one of the first and second hydrogel precursors is a cross-linker. In embodiments, at least one of the first and second hydrogel precursors is a macromolecule, and may be referred to herein as a "functional polymer".

Each of the first and second hydrogel precursors may be multifunctional, meaning that it may include two or more electrophilic or nucleophilic functional groups, such that, for example, a nucleophilic functional group on the first hydrogel precursor may react with an electrophilic functional group on the second hydrogel precursor to form a covalent bond. At least one of the first or second hydrogel precursors includes more than two functional groups, so that, as a result of electrophilic-nucleophilic reactions, the precursors combine to form cross-linked polymeric products.

In embodiments, a multifunctional nucleophilic polymer such as trilysine may be used as a first hydrogel precursor and a multifunctional electrophilic polymer such as a multi-arm PEG functionalized with multiple NHS groups may be used as a second hydrogel precursor. In embodiments, each arm of a multi-armed precursor may be formed of a polyethylene glycol having a molecular weight from about 250 to about 5000, in embodiments from about 1250 to about 2500, in embodiments about 1875. In embodiments, the multi-arm PEG functionalized with multiple NHS groups can, for example, have four, six or eight arms and a total molecular weight of from about 5,000 to about 25,000, in embodiments from about 10,000 to about 20,000, in embodiments about 15,000. Other examples of suitable first and second hydrogel precursors are described in U.S. Pat. Nos. 6,152,943; 6,165,201; 6,179,862; 6,514,534; 6,566,406; 6,605,294; 6,673,093; 6,703,047; 6,818,018; 6,887,974; 7,009,034; 7,332,566; and 7,347,850, the entire disclosures of each of which are incorporated herein by reference.

In embodiments, one or more precursors having biodegradable linkages present in between functional groups may be included to make the hydrogel biodegradable or absorbable. In some embodiments, these linkages may be, for example, esters, which may be hydrolytically degraded in physiological solution. The use of such linkages is in contrast to protein linkages that may be degraded by proteolytic action. A biodegradable linkage optionally also may form part of a water soluble core of one or more of the precursors. Alternatively, or in addition, functional groups of precursors may be chosen such that the product of the reaction between them results in a biodegradable linkage. For each approach, biodegradable linkages may be chosen such that the resulting biodegradable biocompatible crosslinked polymer degrades or is absorbed in a desired period of time. Generally, biodegradable linkages may be selected that degrade the hydrogel under physiological conditions into non-toxic or low toxicity products.

In embodiments the precursors used to form the components of an osmotic pump may also include an initiator. An initiator may be any precursor or group capable of initiating a polymerization reaction for the formation of the in situ forming material.

Hydrogel Swellability

It has been found that changing the length of the arms on a precursor while holding other properties generally constant can alter the swelling properties of the resultant gel from one that swells to one that shrinks. At any given concentration of reactive polymer, an arm length can be utilized that provides for a low-swelling gel with minimal compromise of other properties of the hydrogel. Without being bound to a particular theory, changing the arm length can approximate the distance between crosslinks at equilibrium swelling. The closer the arm length is to equilibrium crosslink distance, the less the arms extend in response to swelling.

As described herein, hydrogels may be made with a low, or even negative, amount of swelling. Such low swelling hydrogels may be useful in forming a housing of an osmotic pump. In contrast, hydrogels which lack low-swelling properties may be suited for use as the pump inside the housing.

Thus, desirable hydrogels herein can include low-swelling hydrogels with desirable reaction time, density, strength, and medical properties. Such low-swelling hydrogels may be formed using precursors having a desirable molecular weight range, solubility, arm-length, chemical composition, chemical structure, chemical composition, density, concentration, arm number, and with desired functional groups and buffers. Some of these parameters are interrelated, so that the choice of one range of starting properties or materials can affect the choice of other properties and materials.

Unless otherwise indicated, swelling of a hydrogel relates to its change in volume (or weight) between the time of its formation, when crosslinking is effectively complete, and the time after being placed in a physiological solution in an unconstrained state for twenty-four hours, at which point it may be reasonably assumed to have achieved its equilibrium swelling state. In embodiments, crosslinking is effectively complete within no more than about fifteen minutes, and often within a few seconds, such that the initial weight can be reasonably noted as "Weight at initial formation."

Accordingly, the following formula I may be used to determine swelling:

$$\% \text{ swelling} = [(\text{Weight at 24 hours} - \text{Weight at initial formation})/\text{Weight at initial formation}]*100 \quad (I)$$

Low-swellable or low-swelling hydrogels of the present disclosure may have a weight upon polymerization that increases no more than about 50% by weight upon exposure to a physiological solution, or that shrink (decrease in weight and volume), e.g., by about 5% or more. This is contrary to other hydrogels, which may experience swelling in amounts of from about 200% to about 600% by weight upon exposure to a physiological solution. Embodiments include, for example, low-swelling hydrogels that have a weight increase from formation to equilibrium hydration of no more than from about 0% to about 50%, in embodiments from about 10% to about 40%, or swell from about 0% to about 50% in volume, in embodiments from about 5% to about 40% in volume, or shrink by a weight decrease of from about 1% to about 50%, in embodiments from about 5% to about 30%. Again, swelling or shrinking is determined by the change in weight of the hydrogel upon exposure to a physiological solution utilizing the formula set forth above.

In some embodiments, shrinkage may be referred to herein as a negative % swelling; thus, in embodiments, a hydrogel of the present disclosure, including a hydrogel used to form the housing of an osmotic pump, may swell, i.e., experience a change in size, from about −50% to about 50% by weight, in other embodiments from about −20% to about 40% by weight. Artisans will immediately appreciate that all values within or otherwise relating to these explicitly articulated limits are disclosed herein.

The weight of the hydrogel includes the weight of the solution in the hydrogel. A hydrogel formed in a location wherein it is constrained is not necessarily a low-swelling hydrogel. For instance, a swellable hydrogel created within the housing of an osmotic pump of the present disclosure may be constrained from swelling by the housing, but nonetheless may be a highly swellable hydrogel, as evidenced by measurements of its swelling when unconstrained and/or the forces against a constraint, i.e., the housing. Such hydrogels may swell in amounts of from about 40% to about 600% by weight, in embodiments from about 100% to about 400% by weight.

The solids content of the hydrogel which has crosslinked and is at equilibrium can affect its mechanical properties and biocompatibility and reflects a balance between competing requirements. In general, a relatively low solids content may be desirable, e.g., from about 5% to about 25% of the combined weight of the hydrogel in an aqueous solution, in embodiments from about 10% to about 20%.

Preparation of Polymers

The reaction conditions for forming crosslinked polymeric hydrogels will depend on the nature of the functional groups. In embodiments, reactions may be conducted in buffered aqueous solutions at a pH of from about 5 to about 12, in embodiments from about 6 to about 10. Buffers include, for example, sodium borate buffer (pH 10) and triethanol amine buffer (pH 7). In some embodiments, organic solvents such as ethanol or isopropanol may be added to improve the reaction speed or to adjust the viscosity of a given formulation.

When the crosslinker and functional polymers are synthetic (for example, when they are based on polyalkylene oxide), it may be desirable to use molar equivalent quantities of the reactants. In some cases, molar excess of a crosslinker may be added to compensate for side reactions such as reactions due to hydrolysis of the functional group.

Synthetic crosslinked gels degrade due to hydrolysis of the biodegradable region. The degradation of gels containing synthetic peptide sequences will depend on the specific enzyme and its concentration. In some cases, a specific enzyme may be added during the crosslinking reaction to accelerate the degradation process.

When choosing the crosslinker and crosslinkable polymer, at least one of the polymers may have more than two functional groups per molecule and at least one degradable region, if it is desired that the resultant biocompatible crosslinked polymer be biodegradable. In embodiments, each biocompatible crosslinked polymer precursor may have more than two functional groups, and in some embodiments, more than four functional groups.

The crosslinking density of the resultant biocompatible crosslinked polymer may be controlled by the overall molecular weight of the crosslinker and functional polymer and the number of functional groups available per molecule. A lower molecular weight between crosslinks, such as 600 Daltons (Da), will give much higher crosslinking density as compared to a higher molecular weight, such as 10,000 Da. Elastic gels may be obtained with higher molecular weight functional polymers with molecular weights of more than 3,000 Da.

The crosslinking density may also be controlled by the overall percent solids of the crosslinker and functional polymer solutions. Increasing the percent solids increases the probability that an electrophilic group will combine with a nucleophilic group prior to inactivation by hydrolysis. Yet another method to control crosslink density is by adjusting the stoichiometry of nucleophilic groups to electrophilic groups. A one to one ratio may lead to the highest crosslink density, however, other ratios of reactive functional groups (e.g., electrophile:nucleophile) are envisioned to suit a desired formulation.

Biodegradable crosslinkers or small molecules as described above may be reacted with proteins, such as albumin, other serum proteins, or serum concentrates to generate crosslinked polymeric networks. Generally, aqueous solutions of crosslinkers may be mixed with concentrated solutions of proteins to produce a crosslinked hydrogel. The reaction may be accelerated by adding a buffering agent, e.g., borate buffer or triethanol amine, during the crosslinking step.

The resulting crosslinked hydrogel's degradation depends on the degradable segment in the crosslinker as well as degradation by enzymes. In the absence of any degradable enzymes, the crosslinked polymer may degrade solely by hydrolysis of the biodegradable segment. In embodiments in which polyglycolate is used as the biodegradable segment, the crosslinked polymer may degrade in from about 1 day to about 30 days depending on the crosslinking density of the network. Similarly, in embodiments in which a polycaprolactone based crosslinked network is used, degradation may occur over a period of from about 1 month to about 8 months. The degradation time generally varies according to the type of degradable segment used, in the following order: polyglycolate<polylactate<polytrimethylene carbonate<polycaprolactone. Thus, it is possible to construct a hydrogel with a desired degradation profile, from a few days to months, using a proper degradable segment.

The hydrophobicity generated by biodegradable blocks such as oligohydroxy acid blocks or the hydrophobicity of PPO blocks in PLURONIC or TETRONIC polymers may be helpful in dissolving small organic drug molecules. Other properties which will be affected by incorporation of biodegradable or hydrophobic blocks include: water absorption, mechanical properties and thermosensitivity.

Polymerization

Formulations may be prepared that are suited to make precursor crosslinking reactions occur in situ, or ex vivo. In general, this may be accomplished by having a precursor that can be activated at the time of application to form a crosslinked hydrogel. Activation can be made before, during, or after application of the precursor, provided that the precursor is allowed to form the osmotic pump's housing and/or form a hydrogel within the housing before crosslinking and associated gelation is otherwise too far advanced. Activation includes, for instance, triggering a polymerization process, initiating a free radical polymerization, or mixing precursors with functional groups that react with each other. Thus, in situ polymerization includes activation of chemical moieties to form covalent bonds to create an insoluble material, e.g., a hydrogel, at a location where the material is to be placed within a patient. In situ polymerizable polymers may be prepared from precursors that can be reacted such that they form a polymer within the patient. Thus precursors with electrophilic functional groups can be mixed or otherwise activated in the presence of precursors with nucleophilic functional groups. In other embodiments, precursors with ethylenically unsaturated groups can be initiated to polymerize in situ in a patient.

In yet other embodiments, as noted above, the formation of a hydrogel to be used as the housing of an osmotic pump, and/or the hydrogel used within the housing, may be formed ex vivo, in the same manner described above for in situ formation.

With respect to forming an osmotic pump housing, and without limiting the present disclosure to a particular theory of operation, it is believed that reactive precursor species that crosslink quickly after combination may form a three dimensional structure that is mechanically interlocked. This interlocking contributes to adherence to tissue, intimate contact, and continuous coverage, especially when formed in situ. The crosslinking reaction leading to gelation can occur, in some embodiments within a time from about 1 second to about 5 minutes, in embodiments from about 3 seconds to about 1 minute; persons of ordinary skill in these arts will immediately appreciate that all values within these explicitly stated ranges are contemplated. For example, in embodiments, the in situ gelation time of hydrogels according to the present disclosure is less than about 20 seconds, and in some embodiments, less than about 10 seconds, and in yet other embodiments less than about 5 seconds. In embodiments where electrophilic precursors are used, such precursors may react with free amines in tissue, thereby serving as a means for attaching the hydrogel utilized to form the housing of an osmotic pump to tissue.

Preparation of Biodegradable Osmotic Pump Implant

The osmotic pump of the present disclosure may include two components, both a biodegradable housing and a hydrogel "pump" within the housing. In embodiments the housing, the pump, or both, may include a bioactive agent. The biodegradable housing of the osmotic pump acts as a shell or frame around the hydrogel pump. In embodiments, the biodegradable housing may be semi-permeable or impermeable.

The housing may be formed in vivo, or the housing may be formed ex vivo, and subsequently introduced in vivo. In embodiments, the housing of the osmotic pump may be formed ex vivo, and then introduced into a patient. For example, a hydrogel may be formed, optionally dehydrated, and the dehydrated or hydrated hydrogel may then be introduced into a patient. Alternatively, the hydrogel forming the housing may be formed in vivo. However formed, once the hydrogel forming the housing, sometimes referred to herein as a "pouch," has been formed, the housing may then be filled with a second hydrogel, in embodiments containing a bioactive agent.

As noted above, in embodiments the biodegradable housing may be formed from a low-swelling or non-swelling polymer. The low-swelling or non-swelling hydrogel polymer of the housing may swell and/or expand in an amount from about −50% to about 50%, in embodiments from about 0% to about 10%, or in other embodiments from about 30% to about 40%. The non-swelling polymer or low-swelling polymer may be, for example, a hydrogel polymer formed from a first hydrogel precursor having multiple amine groups and a second hydrogel precursor formed from a multi-armed precursor possessing a core as described above and from about 3 to about 12 arms, the arms each including a polyethylene glycol having a molecular weight from about 250 to about 5000, in embodiments from about 1250 to about 2,500, in embodiments about 1875. The second hydrogel precursor may have second functional groups at the ends of its arms, capable of reacting with the first precursor. Such low-swelling and non-swelling polymers are described in U.S. Patent Application Publication Nos. 2008/0220047, 2009/0227689, and 2009/0227981, the entire disclosures of each of which are incorporated by reference herein.

In embodiments, the biodegradable housing may then be coated with one or more layers of a biodegradable polymer. The polymer used for the coating may be the same or different from the polymer forming the housing. The coating polymer may be, for example, oxidized cellulose, polylactide, polyglycolide, polylactide-co-glycolide copolymers, combinations thereof, and the like. In embodiments, the coating may be a molecular weight cut off membrane. As used herein, a molecular weight cut off membrane is a semi-permeable membrane possessing pore sizes that will prevent passage of particles having a minimum molecular weight and/or size. In embodiments, the hydrogel pouch may be coated with one or more layers of a biodegradable coating following implantation.

In embodiments, the biodegradable housing may be filled with a swellable hydrogel. As noted above, the swellable hydrogel forming the "pump" may swell, for example, from about 40% to about 600%, in embodiments from about 100% to about 400%. Examples of swellable hydrogels include COSEAL® (Angiotech Pharmaceuticals), and DURASEAL® (Confluent Surgical, Inc).

The swellable hydrogel may contain a bioactive agent. The bioactive agent may be suspended in pure form in the hydrogel or may be encapsulated and suspended in the hydrogel. If encapsulated, the bioactive agent may be in microspheres, vesicles, liposomes, nanospheres, combinations thereof, and the like. The release rate of the bioactive agent may be further controlled by the extent of swelling of the hydrogel.

In embodiments, one or more layers of the biodegradable housing includes a bioactive agent. The bioactive agents in the layers of the housing may move into the hydrogel within the housing of the osmotic pump via osmosis. The bioactive agent may thus be released as the housing degrades.

In other embodiments, the bioactive agent may diffuse through the housing. The biodegradable housing may also include an opening through which a bioactive agent may exit.

In yet other embodiments, an osmotic pump of the present disclosure may include a dehydrated hydrogel within an impermeable housing, such as one fashioned of poly-1-lactide or polylactide-polyglycolide copolymers. The impermeable housing may possess at least one opening permitting entry of biological fluids into the osmotic pump and hydration of the dehydrated hydrogel, which will swell upon contact with the biological fluids and may release any bioactive agent therefrom. Once the hydrogel has swollen, it may block the at least one opening previously permitting entry of biological fluids into the osmotic pump, thus reducing release of bioactive agent from the osmotic pump. In use, with decrease entry of biological fluids into the pump, the hydrogel may then begin to shrink. Additional bioactive agent may then be released as additional biological fluid enters the osmotic pump. The entry of biological fluid into the osmotic pump may once again swell the hydrogel therein. In this way, a pulse like release of a bioactive agent may be achieved.

Referring now in specific detail to the Figures, in which like numbers identify similar or identical elements, FIG. 1 represents an embodiment of an osmotic pump 10 of the disclosure. A housing 12, sometimes referred to herein as pouch, may be formed, for example, from two layers 14 and 16. The material forming the layers 14, 16 may be the same or different, for example, outer layer 14 may be an oxidized cellulose/polylactide coating formed on inner hydrogel layer 16. Although only one outer layer 14 is shown, outer layer 14 may include many layers made from the same or different materials. In embodiments, the outer layer 14 may be a molecular weight cut off membrane capable of preventing exit of certain sized molecules, such as larger bioactive agents, from the pouch 12. Inner layer 16 may be formed from, for example, a non-swelling hydrogel, including those disclosed in U.S. Patent Application Publication No. 2008/0220047, the entire disclosure of which is incorporated by reference herein. The pouch 12 may be preformed and introduced into a patient prior to filling. In embodiments, the pouch 12 may be formed in situ.

Pouch 12 may then be filled with a hydrogel 18. The hydrogel 18 may contain a bioactive agent 20. The hydrogel 18 may absorb liquid from the in situ environment and expand within the pouch 12 forcing the bioactive agent 20 through opening 22. In embodiments, outer layer 14 may be a molecular weight cut off membrane capable of preventing a larger bioactive agent 20, such as a protein, from eluting through pouch 12, forcing the bioactive agent 20 through opening 22.

In embodiments, as noted above, a bioactive agent 20 may be located in one or more layers 14, 16, of pouch 12. As liquid is drawn through pouch 12 into the hydrogel 18, the bioactive agent 20 may be carried into the hydrogel 18 prior to being forced out through opening 22. This additional step further controls the release rate of the bioactive agent 20.

Osmotic pumps of the present disclosure may be of any other suitable shape and configuration. For example, osmotic pumps may be circular, discs, rods, cylinders, capsules, spheres, ovoids, pinwheels, nautilus, combinations thereof, and the like.

Figure 2:
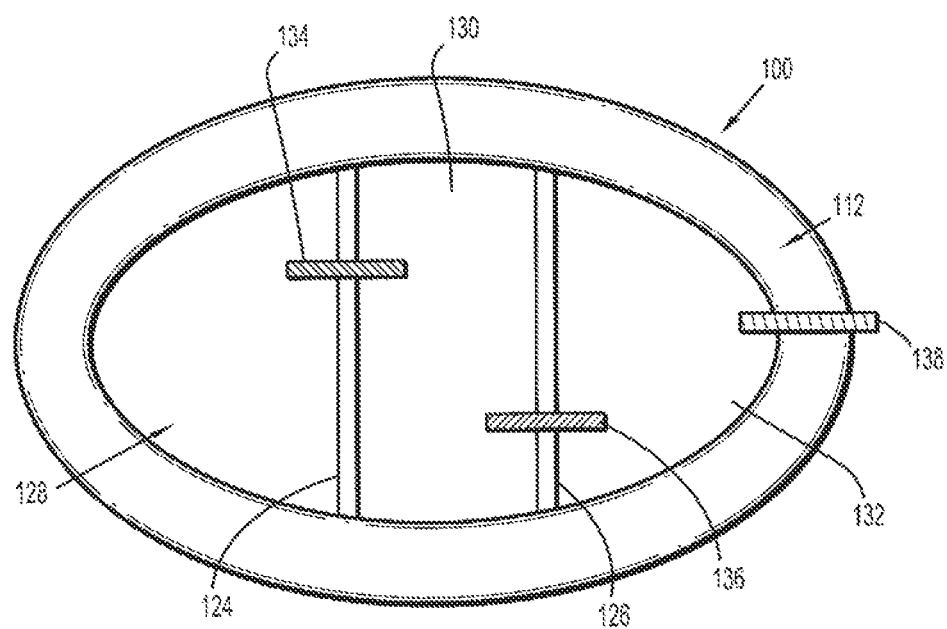
FIG. 2 represents an alternate embodiment of an osmotic pump of the present disclosure.

For example, turning to FIG. 2, an alternate embodiment of an osmotic pump 100 of the disclosure is presented therein, including housing or pouch 112. Pouch 112 may include two barriers therein, 124 and 126, formed from the same material as the housing 112. Barriers 124 and 126 thus form three different compartments, 128, 130 and 132, within housing 112. These compartments, in turn, may then be filled with a hydrogel possessing a bioactive agent (not shown). Housing 112, and barriers 124 and 126, may also possess degradable regions 138, 134 and 136, respectively. Degradable regions 134, 136, and 138, in embodiments, may be formed of a degradable material, such as a degradable suture material, predegraded sutures, or sutures with varying degradation rates. The degradation rates of degradable regions 134, 136 and 138 may be the same or different. In embodiments, degradable region 138 may degrade faster than degradable region 136 which, in turn, may degrade faster than region 134. Degradation of degradable regions 134, 136 and 138 may thus be tailored to release the bioactive agent from osmotic pump 100. For example, where degradable region 138 degrades faster than degradable region 136, a bioactive agent in a hydrogel in compartment 132 may be released from osmotic pump 100 prior to the release of any bioactive agent contained in the hydrogel in compartments 130 and/or 128. Similarly, if degradable region 136 degrades faster than degradable region 134, any bioactive agent in a hydrogel in compartment 130 may be released from osmotic pump 100 prior to the release of any bioactive agent contained in the hydrogel in compartment 128.

Similarly, different hydrogels may be present in compartments 128, 130 and 132, with each hydrogel having a different release profile of a bioactive agent included therein. Varying the hydrogel components in compartments 128, 130 and 132 may thus further be used to tailor the release of bioactive agents from osmotic pump 100.

Osmotic pump 100 may be suitable, in embodiments, for vitamin and/or hormone therapy. For example, vitamin B12 could be released therefrom over a period of several weeks, by tailoring the degradation rates of the materials utilized to form degradable regions 134, 136 and 138. Similarly, testosterone, estrogen, or both, may be released at varying rates over a period of several weeks, by tailoring the degradation rates of the materials utilized to form degradable regions 134, 136 and 138. Likewise, osmotic pump 100 may be used as a birth control device, with varying releases of estrogen and a progestin. In embodiments, the osmotic pump of FIG. 2 may be used for pulsatile or sequential delivery of bioactive agents.

Figure 3:
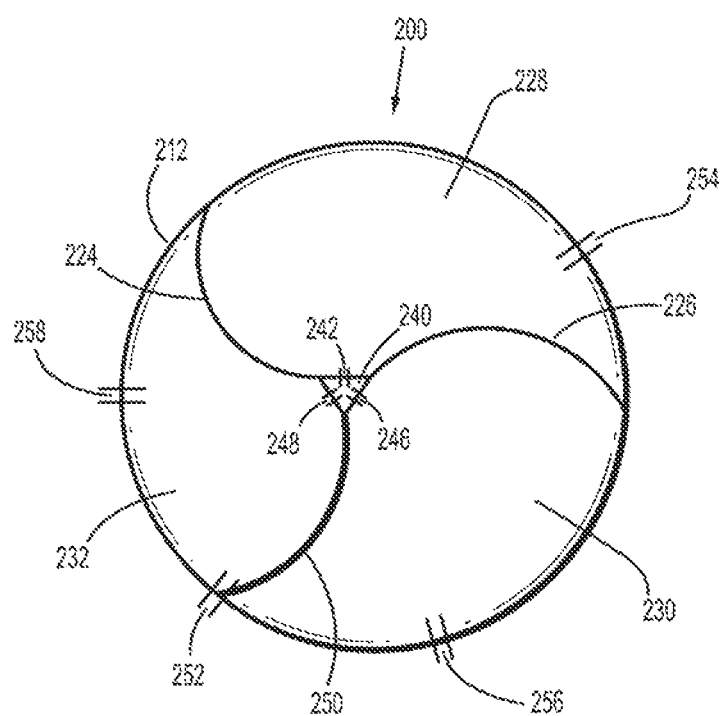
FIG. 3 represents an alternate embodiment of an osmotic pump of the present disclosure having a pinwheel configuration.

Turning now to FIG. 3, an alternate embodiment of an osmotic pump 200 of the disclosure, having a pinwheel configuration, is presented therein. Osmotic pump 200 may include a housing or pouch 212 which, in turn, may include two barriers therein, 224 and 226, and an additional barrier/channel 250, formed from the same material as the housing 212. Barriers 224, 226 and barrier/channel 250 thus form three different compartments, 228, 230 and 232, within housing 212. These compartments, in turn, may then be filled with a hydrogel possessing a bioactive agent (not shown).

At the center of osmotic pump 200 is a mixing chamber 240, possessing openings 242, 246 and 248 connecting mixing chamber 240 with compartments 228, 230 and 232, respectively. In use, bioactive agents in the hydrogels found in compartments 228, 230 and 232 may travel through openings 242, 246 and 248 into mixing chamber 240, whereby they may mix and then be released from osmotic pump 200 by passing through barrier/channel 250 for release at opening 252. The hydrogels utilized in compartments 228, 230 and 232 may have varying release rates of bioactive agents therein, thus permitting one to tailor the release of bioactive agents therefrom.

The degree of mixing and speed with which bioactive agents may be introduced into mixing chamber 240 may be influenced by blocking openings 242, 246 and/or 248 with a degradable material, such as a different hydrogel and/or a degradable suture type material, thereby allowing one to tailor the passage of bioactive agents into the mixing chamber 240. Degradable materials used to block openings 242, 246 and 248 may be the same or different, and may have varying degradation rates, permitting the release of drug(s) over time. Similarly, passage of bioactive agents through barrier/channel 250 for release at opening 252 may be influenced by blocking opening 252 with a degradable material, such as a different hydrogel and/or a degradable suture type material, thereby allowing one to further tailor the passage of bioactive agents from osmotic pump 200.

In yet additional embodiments, additional openings 254, 256, and 258 may be in housing 212, permitting additional release of bioactive agents from compartments 228, 230, and 232 of osmotic pump 200.

Osmotic pump 200 may be suitable, in embodiments, for the release of multiple drugs, sometimes referred to, for example, as drug cocktails, which are suitable for treatment of various diseases, including Acquired Immune Deficiency Syndrome (AIDS). For example, azidothymidine (AZT), dideoxycytidine (DDC) and didanosine (DDI) may be introduced into the hydrogels contained within compartments 228, 230, and 232, respectively, and then mixed and released from osmotic pump 200 as described above. In embodiments, the pump of FIG. 3 may be used for the concurrent delivery of drug(s).

Figure 4:
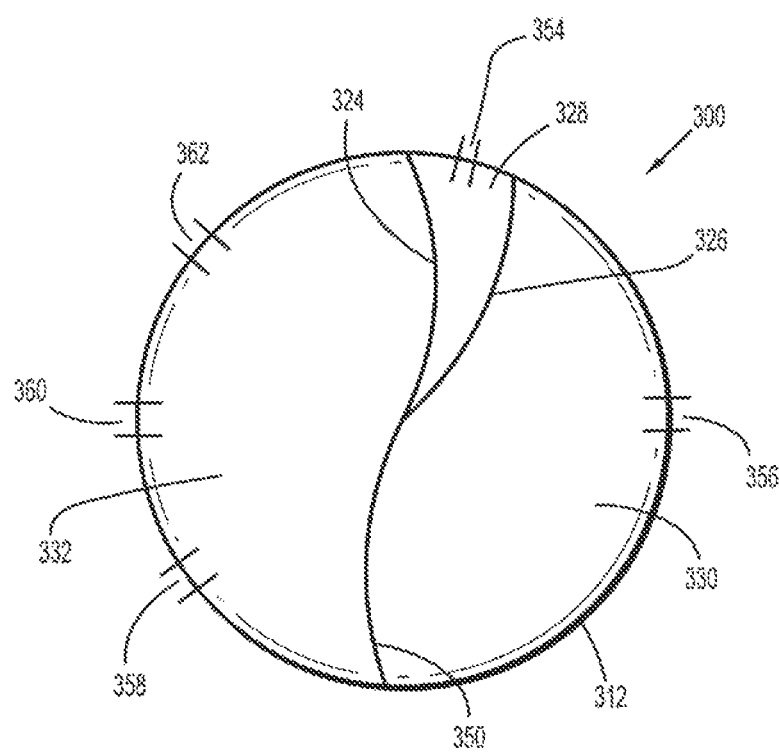
FIG. 4 represents an alternate embodiment of an osmotic pump of the present disclosure having a pinwheel configuration.

FIG. 4 is an alternate embodiment of an osmotic pump 300 of the disclosure, also having a pinwheel configuration. Osmotic pump 300 includes a housing or pouch 312 which, in turn, may include three barriers therein, 324, 326, and 350, formed from the same material as the housing 312. Barriers 324, 326 and 350 thus form three different compartments, 328, 330 and 332, within housing 312. These compartments, in turn, may then be filled with a hydrogel possessing a bioactive agent (not shown).

Openings 354, 356, 358, 360, and 362 may be in housing 312, permitting release of bioactive agents from compartments 328, 330, and 332. The degree of release of the bioactive agent from compartments 328, 330 and 332 may be influenced by blocking openings 354, 356, 358, 360, and 362 with a degradable material, such as a different hydrogel and/or a degradable suture type material, thereby allowing one to tailor the release of bioactive agents from compartments 328, 330, and 332. The hydrogels utilized in compartments 328, 330 and 332 may also have varying release rates of bioactive agents therein, thus further permitting one to tailor the release of bioactive agents therefrom. Moreover, as depicted in FIG. 4, where one of the compartments is larger and thus contains a greater volume of hydrogel and more bioactive agent therein, that compartment (e.g. 332 in FIG. 4), may possess multiple openings (e.g., 358, 360 and 362).

Osmotic pump 300 may be suitable, in embodiments, for supplemental hormone therapy, for example, for the treatment of hypogonadal women. For example, compartment 328 could include testosterone, compartment 330 could include a progestin, and compartment 332 could include estradiol. In embodiments, the pump of FIG. 4 may be used for concurrent delivery of drug(s).

Figure 5:
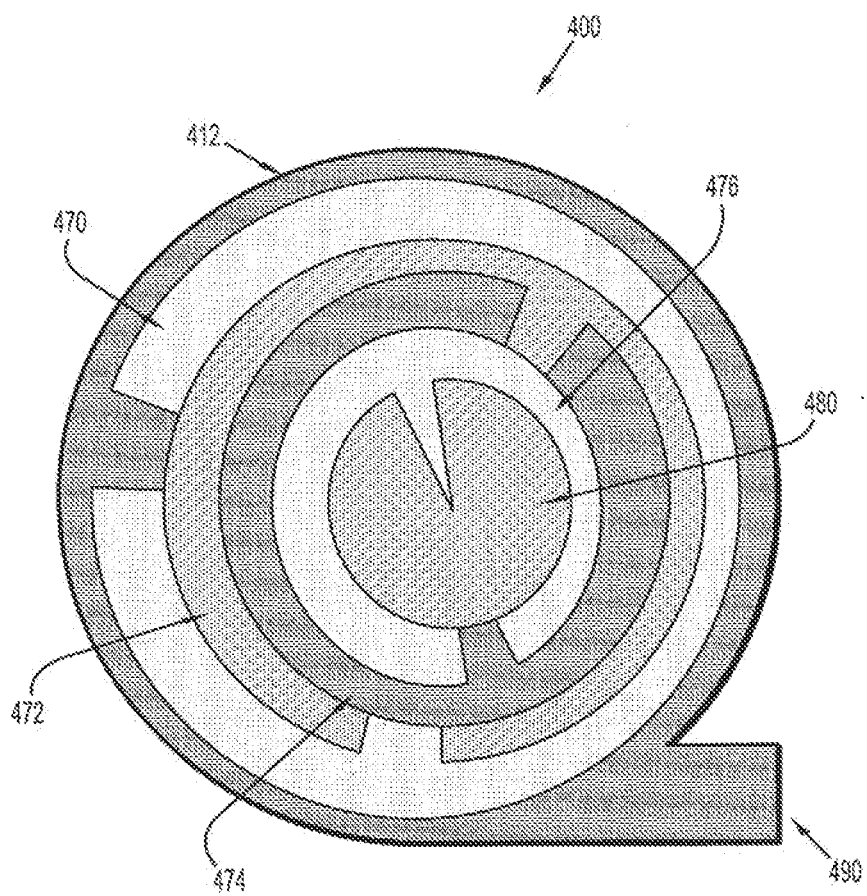
FIG. 5 represents an alternate embodiment of an osmotic pump of the present disclosure having a nautilus configuration.

An alternate embodiment of an osmotic pump of the present disclosure is presented in FIG. 5, which depicts an osmotic pump 400 having a nautilus configuration. Osmotic pump 400 may include a housing or pouch 412, which, in turn, may include barriers therein forming the nautilus configuration. The osmotic pump 400 may thus include multiple layers of the same or different drugs in the same or different hydrogels, including hydrogel layers 470, 472, 474, 476, surrounding core 480. In embodiments, rather than including a bioactive agent of drug in layers 470, 472, 474, 476, one of the layers may be a drug-free biomaterial, such as polylactic acid. Opening 490 permits release of bioactive agents from osmotic pump 400. The hydrogels utilized in layers 470, 472, 474, and 476, as well as core 480, may have varying release rates of bioactive agents, thus permitting one to tailor the release of bioactive agents therefrom. The gels, in embodiments, permit the release of bioactive agents as they degrade, with those hydrogels closer to opening 490 degrading prior to the others so that the drug(s) are released from pump 400 sequentially as the various hydrogels degrade over time. Thus, for example, hydrogel 470 may degrade first in time, releasing any bioactive agent therein through opening 490, followed by degradation of hydrogel 472, which will release any bioactive agent therein through opening 490, followed by degradation of hydrogel 474 and its release of any bioactive agent therein through opening 490, followed by degradation of hydrogel 476 and its release of any bioactive agent therein through opening 490, followed by degradation of core 480 and its release of any bioactive agent therein through opening 490.

Visualization Agents

The precursor and/or the crosslinked polymer may contain visualization agents to improve their visibility. Visualization agents may be selected from a variety of non-toxic colored substances, such as dyes, suitable for use in implantable medical devices. Suitable dyes are within the purview of those skilled in the art and may include, for example, a dye for visualizing a thickness of the hydrogel as it is formed in situ, e.g., as described in U.S. Pat. No. 7,009,034. In some embodiments, a suitable dye may include, for example, FD&C Blue #1, FD&C Blue #2, FD&C Blue #3, FD&C Blue #6, D&C Green #6, methylene blue, indocyanine green, other colored dyes, and combinations thereof. It is envisioned that additional visualization agents may be used such as fluorescent compounds (e.g., fluorescein or eosin), x-ray contrast agents (e.g., iodinated compounds), ultrasonic contrast agents, and MRI contrast agents (e.g., Gadolinium containing compounds).

The visualization agent may be present in either a crosslinker or functional polymer solution. The colored substance may or may not become incorporated into the biocompatible crosslinked polymer. In embodiments, however, the visualization agent does not have a functional group capable of reacting with the crosslinker or functional polymer.

The visualization agent may be used in small quantities, in embodiments less than 1% weight/volume, and in other embodiments less that 0.01% weight/volume and in yet other embodiments less than 0.001% weight/volume concentration.

Delivery of Bioactive Agents

The subject precursors, such as the crosslinkers and functional polymers described above, as well as their reaction products, may be used for drug therapy or delivery of bioactive agents. The bioactive agent may be attached to or incorporated within a hydrogel used to form the housing of an osmotic pump of the present disclosure, as well as the hydrogel within the housing of an osmotic pump of the present disclosure.

As used herein, a bioactive agent includes any active pharmaceutical ingredient or drug that provides a therapeutic or prophylactic effect, a compound that affects or participates in tissue growth or cell differentiation, a compound that may be able to invoke a biological action such as an immune response or that may play any other role in one or more biological processes may be used. Biologically active agents or drug compounds that may be added and delivered from the crosslinked polymer or gel include: proteins, glycosaminoglycans, carbohydrates, nucleic acid, and inorganic and organic biologically active compounds.

Examples of drugs and alternative forms of these drugs such as salt forms, free acid forms, free base forms, and hydrates include: antimicrobials (e.g., cephalosporins such as cefazolin sodium, cephradine, cefaclor, cephapirin sodium, ceftizoxime sodium, cefoperazone sodium, cefotetan disodium, cefuroxime azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium); penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium); erythromycins (e.g., erythromycin ethylsuccinate, erythromycin, erythromycin estolate, erythromycin lactobionate, erythromycin stearate, and erythromycin ethylsuccinate); and tetracyclines (e.g., tetracycline hydrochloride, doxycycline hyclate, and minocycline hydrochloride, azithromycin, and clarithromycin); analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); anesthetics; antiepileptics; antihistamines; non-steroidal anti-inflammatories (e.g., indomethacin, ketoprofen, flurbiprofen, naproxen, ibuprofen, ramifenazone, and piroxicam); steroidal anti-inflammatories (e.g., cortisone, dexamethasone, fluazacort, celecoxib, rofecoxib, hydrocortisone, prednisolone, and prednisone); cardiovascular drugs (e.g., coronary vasodilators and nitroglycerin); diagnostic agents; cholinomimetics; antimuscarinics; muscle relaxants; adrenergic neuron blockers; neurotransmitters; antineoplastics (e.g., cyclophosphamide, actinomycin, bleomycin, daunorubicin, doxorubicin hydrochloride, epirubicin, mitomycin, methotrexate, fluorouracil, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, tamoxifen, and piposulfan,); immunogenic agents; immunosuppressants (e.g., cyclosporine, azathioprine, mizoribine, and FK506 (tacrolimus)); gastrointestinal drugs; diuretics; lipids; lipopolysaccharides; polysaccharides; enzymes; non-steroidal antifertility agents; parasympathomimetic agents; psychotherapeutic agents; psychoactive drugs; tranquilizers; decongestants; sedative hypnotics (e.g., barbiturates such as pentobarbital and secobarbital); and benzodiazepines such as flurazepam hydrochloride, triazolam, and midazolam); steroids; sulfonamides; vitamins; antimalarials; anti-migraine agents (e.g., ergotamine, propanolol, isometheptene mucate, and dichloralphenazone); anti-parkinson agents (e.g., L-Dopa and ethosuximide); antitussives; bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate); anticholinergic agents (e.g., oxybutynin and ipratropium bromide); xanthines (e.g., aminophylline, dyphylline, metaproterenol sulfate, and aminophylline); mast cell stabilizers (e.g., cromolyn sodium); inhalant corticosteroids (e.g., beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; flunisolide; and fluticasone proprionate); angiogenic agents; anti-angiogenic agents; alkaloids; analgesics; narcotics (e.g., codeine, dihydrocodeinone, meperidine, morphine, and the like); opoid receptor antagonists (e.g., naltrexone and naloxone); anti-cancer agents; chemotherapeutic drugs; anti-convulsants; anti-emetics (e.g., meclizine hydrochloride, nabilone, prochlorperazine, dimenhydrinate, promethazine hydrochloride, thiethylperazine, and scopolamine); antihistimines (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, and methdilazine); anti-inflammatory agents (e.g., hormonal agents, hydrocortisone, non-hormonal agents, allopurinol, indomethacin, phenylbutzone and the like); prostaglandins and cytotoxic drugs; drugs affecting reproductive organs; estrogens; antibacterials (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antibodies; antibiotics (e.g., neomycin, streptomycin, chloramphenicol, cephalosporin, ampicillin, penicillin, tetracycline, and ciprofloxacin); anti-fungals (e.g., griseofulvin, ketoconazole, itraconizole, amphotericin B, nystatin, and candicidin); anti-virals (e.g., interferon alpha, beta or gamma, zidovudine, amantadine hydrochloride, ribavirin, and acyclovir); anticoagulants (e.g., heparin, heparin sodium, and warfarin sodium); antidepressants (e.g., nefopam, oxypertine, doxepin, amoxapine, trazodone, amitriptyline, maprotiline, phenylzine, desipramine, nortriptyline, tranylcypromine, fluoxetine, doxepin, imipramine, imipramine pamoate, isocarboxazid, trimipramine, and protriptyline); immunological agents; antiasthamatics (e.g., ketotifen and traxanox); antidiabetics (e.g., biguanides and sulfonylurea derivatives); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); antianginal agents (e.g., beta-adrenergic blockers; calcium channel blockers (e.g., nifedipine and diltiazem); nitrates (e.g., nitroglycerin, isosorbide dinitrate, pentaerythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encamide, digoxin, digitoxin, mexiletine, disopyramide phosphate, procainamide, quinidine sulfate, quinidine gluconate, quinidine polygalacturonate, flecamide acetate, tocamide, and lidocaine); antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium); antigout agents (e.g., colchicine and allopurinol); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenyloin, phenyloin sodium, clonazepam, primidone, phenobarbitol, carbamazepine, amobarbital sodium, methsuximide, metharbital, mephobarbital, mephenyloin, phensuximide, paramethadione, ethotoin, phenacemide, secobarbitol sodium, clorazepate dipotassium, and trimethadione); agents useful for calcium regulation (e.g., calcitonin and parathyroid hormone); anti-infectives (e.g., GM-CSF); steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens); progestins (e.g., methoxyprogesterone acetate and norethindrone acetate); corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate); and thyroid hormones (e.g., levothyroxine sodium); hypoglycemic agents (e.g., human insulin, purified beef insulin, purified pork insulin, glyburide, chlorpropamide, glipizide, tolbutamide, and tolazamide); hypolipidemic agents (e.g., clofibrate, dextrothyroxine sodium, probucol, pravastitin, atorvastatin, lovastatin, and niacin); agents useful for erythropoiesis stimulation (e.g., erythropoietin); and anti-ulcer/antireflux agents (e.g., famotidine, cimetidine, and ranitidine hydrochloride).

Other examples of suitable biologically active agents include viruses and cells; peptides; polypeptides and proteins; analogs; bacteriophages; muteins and active fragments thereof, such as immunoglobulins, antibodies, and cytokines (e.g., lymphokines, monokines, and chemokines); blood clotting factors; hemopoietic factors; interleukins (e.g., IL-2, IL-3, IL-4, IL-6); interferons (e.g., β-IFN, (α-IFN and γ-IFN)); erythropoietin; nucleases; tumor necrosis factor; colony stimulating factors (e.g., GCSF, GM-CSF, and MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor and insulin-like growth factor); proteins (e.g., DNase, alginase, superoxide dismutase, and lipase); protein inhibitors, protein antagonists, and protein agonists; nucleic acids (e.g., sense or anti-sense nucleic acids encoding any therapeutically useful protein, including any of the proteins described herein, DNA, and RNA); oligonucleotides; polynucleotides; and ribozymes.

Other bioactive agents useful in the compositions and methods described herein include mitotane, halonitrosoureas, anthrocyclines, ellipticine, ceftazidime, oxaprozin, valacyclovir, famciclovir, flutamide, enalapril, mefformin, itraconazole, gabapentin, fosinopril, tramadol, acarbose, lorazepan, follitropin, omeprazole, lisinopril, tramsdol, levofloxacin, zafirlukast, granulocyte stimulating factor, nizatidine, bupropion, perindopril, erbumine, adenosine, alendronate, alprostadil, betaxolol, bleomycin sulfate, dexfenfluramine, fentanyl, gemcitabine, glatiramer acetate, granisetron, lamivudine, mangafodipir trisodium, mesalamine, metoprolol fumarate, miglitol, moexipril, monteleukast, octreotide acetate, olopatadine, paricalcitol, somatropin, sumatriptan succinate, tacrine, nabumetone, trovafloxacin, dolasetron, finasteride, isradipine, tolcapone, enoxaparin, fluconazole, lansoprazole, pamidronate, didanosine, diclofenac, cisapride, venlafaxine, troglitazone, fluvastatin, losartan, imiglucerase, donepezil, olanzapine, valsartan, fexofenadine, adapalene, doxazosin mesylate, mometasone furoate, ursodiol, felodipine, nefazodone hydrochloride, valrubicin, albendazole, medroxyprogesterone acetate, nicardipine hydrochloride, zolpidem tartrate, rubitecan, amlodipine besylate/benazepril hydrochloride, paroxetine hydrochloride, podofilox, pramipexole dihydrochloride, quetiapine fumarate, candesartan, cilexetil, ritonavir, busulfan, flumazenil, risperidone, carbemazepine, carbidopa, levodopa, ganciclovir, saquinavir, amprenavir, sertraline hydrochloride, clobustasol, diflucortolone, halobetasolproprionate, sildenafil citrate, chlorthalidone, imiquimod, simvastatin, citalopram, irinotecan hydrochloride, sparfloxacin, efavirenz, tamsulosin hydrochloride, mofafinil, letrozole, terbinafine hydrochloride, rosiglitazone maleate, lomefloxacin hydrochloride, tirofiban hydrochloride, telmisartan, diazapam, loratadine, toremifene citrate, thalidomide, dinoprostone, mefloquine hydrochloride, trandolapril, mitoxantrone hydrochloride, tretinoin, etodolac, nelfinavir mesylate, indinavir, nifedipine, cefuroxime, and nimodipine.

In embodiments, the gels of the present disclosure may be utilized to provide pain relief, by administering analgesics, narcotics, etc. In other embodiments, the gels of the present disclosure may be utilized to treat diabetes, through the administration of insulin and other relevant agents. As noted above, gels of the present disclosure may also be utilized in hormone therapy, including supplemental hormone therapy, contraceptives, AIDS treatments, diabetes, treatments for vitamin deficiencies, combinations thereof, and the like.

Applicators

The precursors used to form hydrogels utilized in osmotic pumps of the present disclosure may be placed into solution prior to use, with the solution being delivered to the patient. The hydrogel system solutions should not contain harmful or toxic solvents. In embodiments, the precursors may be substantially soluble in water to allow application in a physiologically-compatible solution, such as buffered isotonic saline. One may use a dual syringe or similar device to apply the precursor solutions, such as those described in U.S. Pat. Nos. 4,874,368; 4,631,055; 4,735,616; 4,359,049; 4,978,336; 5,116,315; 4,902,281; 4,932,942; 6,179,862; 6,673,093; 6,152,943; and 7,347,850.

Generally, two or more crosslinkable components may be applied to form a hydrogel in situ. For example, two crosslinkable precursor solutions, each containing one component of a co-initiating system capable of crosslinking when mixed together, may be placed in separate chambers of an applicator. When the applicator is activated, the emergent contents may contact tissue in vivo or be placed within the housing of an osmotic pump, resulting in mixing and crosslinking of the two solutions to form a hydrogel.

In embodiments, the crosslinkable solutions are stored in separate compartments, e.g., a multi-cylinder syringe, and communicated under pressure to an external orifice for expulsion from the device.

In other embodiments, the osmotic pumps of the present disclosure are formed ex vivo, and then implanted into a patient. Thus, the housing or shell may be first formed ex vivo of a suitable first hydrogel, with the second hydrogel pump placed within the housing, either ex vivo or in vivo. The housing, with or without the hydrogel pump, may be implanted in any suitable shape or form, including capsules, cylinders, rods, spheres, ovoids, pinwheels, nautilus, combinations thereof, and the like. In embodiments, the osmotic pump of the hydrogel may be in the form of a capsule, including a soft gel capsule. The second hydrogel pump may be introduced in the housing ex vivo, so the implant includes both hydrogels. In other embodiments, the hydrogel housing may be implanted in a patient, with the second hydrogel introduced therein by means within the purview of those skilled in the art, including by a syringe, cannula or some similar device which permits introduction of the second hydrogel within the first hydrogel. Placement of the osmotic pump may be subcutaneously, transdermally, intraperitoneally, intramuscularly, combinations thereof, and the like.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 30° C.

EXAMPLES

Example 1

A pouch may be formed using an inner layer of non-swelling or low-swelling polymer and an outer layer of oxidized cellulose/polylactide. The housing may then be filled with a swellable/shrinkable hydrogel formed from a PEG functionalized with N-hydroxysuccinimide groups in combination with trilysine, containing a bioactive agent.

Example 2

A pouch of a non-swelling polymer is formed in situ. The pouch is then filled with a swellable/shrinkable hydrogel formed from a PEG functionalized with N-hydroxysuccinimide groups in combination with trilysine, in which a bioactive agent is suspended. The delivery of the bioactive agent may be driven by the expansion and contraction of the hydrogel.

Example 3

Example 1 is followed except that an additional outer layer of a molecular weight cut off membrane is applied to the pouch.

Example 4

Example 1 is followed except that the non-swelling polymer and/or oxidized cellulose/polylactide layer of the polymer includes a bioactive agent.

Example 5

A pouch may be formed ex vivo using an inner layer of non-swelling polymer and an outer layer of oxidized cellulose/polylactide. The housing may then be filled, either ex vivo or in vivo, with a swellable/shrinkable hydrogel formed from a PEG functionalized with N-hydroxysuccinimide groups in combination with trilysine, containing a bioactive agent such as an analgesic or insulin. The pouch may be in the form of a capsule. The capsule may then be introduced subcutaneously into a patient, where it will release the bioactive agent over time.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments of the present disclosure. Various modifications and variations of the components used to form the surgical implant, as well as methods of delivering the components will be apparent to those skilled in the art from the foregoing detailed description. Such modifications and variations are intended to come within the scope and spirit of the claims appended hereto.

What is claimed is:

1. An implantable drug delivery device comprising:
a biodegradable pouch comprising a biodegradable polymeric material;
at least two barrier layers within the biodegradable pouch, the at least two barrier layers forming at least three compartments within the biodegradable pouch; and
a biodegradable hydrogel within said biodegradable pouch;
wherein the biodegradable hydrogel comprises a bioactive agent, and
wherein each of the at least two barrier layers possess at least one degradable region.

2. The implantable drug delivery device of claim 1, wherein the biodegradable hydrogel within the biodegradable pouch is formed of a first precursor comprising electrophilic groups and a second precursor comprising nucleophilic groups.

3. The implantable drug delivery device of claim 2, wherein the electrophilic groups of the first hydrogel precursor comprise N-hydroxysuccinimides and the nucleophilic groups of the second hydrogel precursor comprise amines.

4. The implantable drug delivery device of claim 1, wherein the biodegradable polymeric material comprises a second hydrogel capable of a changing in size by a weight decrease from about 1% to about 50% or a weight increase from about 0% to about 50%, and the biodegradable hydrogel swells by an amount from about 40% by weight to about 600% by weight.

5. The implantable drug delivery device of claim 1, wherein the biodegradable polymeric material forming the biodegradable pouch comprises a first precursor comprising electrophilic groups and a second precursor comprising nucleophilic groups.

6. The implantable drug delivery device of claim 5, wherein the first precursor comprises a multi-armed precursor possessing a core and arms, the arms each comprising a polyethylene glycol having a molecular weight from about 250 to about 5000.

7. The drug delivery device of claim 6, wherein the core is selected from the group consisting of polyethers, polyamino acids, proteins, and polysaccharides.

8. The implantable drug delivery device of claim 6, wherein the core is selected from the group consisting of polyethylene glycol, polyethylene oxide, polyethylene oxide-co-polypropylene oxide, co-polyethylene oxide copolymers, polyvinyl alcohol, polyvinyl pyrrolidinone, dextran, chitosan, carboxymethylcellulose, oxidized cellulose, derivatives thereof, and combinations thereof.

9. The implantable drug delivery device of claim 5, wherein the nucleophilic groups comprise amines.

10. The implantable drug delivery device of claim 1, wherein the biodegradable polymeric material comprises a low-swelling hydrogel capable of changing in size by a weight decrease from about 5% to about 30% or a weight increase from about 10% to about 40%, and the biodegradable hydrogel swells by an amount from about 100% by weight to about 400% by weight.

11. The implantable drug delivery of claim 1, wherein the biodegradable polymeric material is selected from the group consisting of oxidized cellulose, polylactide, polyglycolide, polylactide-co-glycolide copolymer, and combinations thereof.

12. The implantable drug delivery device of claim 1, wherein the biodegradable pouch further comprises an inner layer and at least one outer layer.

13. The implantable drug delivery device of claim 12, wherein the at least one outer layer is selected from the group consisting of oxidized cellulose, polylactide, polyglycolide, polylactide-co-glycolide copolymer, and combinations thereof.

14. The implantable drug delivery device of claim 12, wherein the at least one outer layer comprises a molecular weight cut off membrane.

15. The implantable drug delivery device of claim 1, wherein the bioactive agent is selected from the group consisting of local anesthetics, vitamins, hormones, and combinations thereof.

16. The implantable drug delivery device of claim 1, wherein the biodegradable pouch is semi-permeable.

17. The implantable drug delivery device of claim 1, wherein the bioactive agent is encapsulated in a polymeric microcapsule.

18. The implantable drug delivery device of claim 1, wherein the implantable drug delivery device possesses a shape selected from the group consisting of circular, discs, rods, cylinders, capsules, spheres, ovoids, pinwheels, nautilus, and combinations thereof.

* * * * *